US009190616B2

(12) United States Patent
Paulasaari et al.

(10) Patent No.: US 9,190,616 B2
(45) Date of Patent: Nov. 17, 2015

(54) ORGANOMETALLIC MONOMERS AND HIGH REFRACTIVE INDEX POLYMERS DERIVED THEREFROM

(75) Inventors: Jyri Paulasaari, Espoo (FI); Juha T. Rantala, Espoo (FI)

(73) Assignee: Silecs Oy, Espoo (FI)

( * ) Notice: Subject to any disclaimer, the term of this patent is extended or adjusted under 35 U.S.C. 154(b) by 0 days.

(21) Appl. No.: 14/126,447

(22) PCT Filed: Jun. 14, 2012

(86) PCT No.: PCT/FI2012/050602
§ 371 (c)(1),
(2), (4) Date: Jun. 12, 2014

(87) PCT Pub. No.: WO2012/172177
PCT Pub. Date: Dec. 20, 2012

(65) Prior Publication Data
US 2014/0288260 A1 Sep. 25, 2014

Related U.S. Application Data

(60) Provisional application No. 61/496,585, filed on Jun. 14, 2011.

(30) Foreign Application Priority Data

Jun. 14, 2011 (FI) .................................. 20115592

(51) Int. Cl.
| H01L 51/00 | (2006.01) |
| C07F 7/18 | (2006.01) |
| C07F 7/30 | (2006.01) |
| C08G 77/392 | (2006.01) |

(52) U.S. Cl.
CPC .......... *H01L 51/0036* (2013.01); *C07F 7/1836* (2013.01); *C07F 7/30* (2013.01); *C08G 77/392* (2013.01); *H01L 51/0074* (2013.01); *H01L 51/0094* (2013.01)

(58) Field of Classification Search
CPC .................................................. H01L 51/0036
USPC ........................................................... 528/25
See application file for complete search history.

(56) References Cited

U.S. PATENT DOCUMENTS

2007/0048532 A1    3/2007    Lyu et al.

FOREIGN PATENT DOCUMENTS

| DE | 19733882 A1 | 2/1999 |
| JP | 2010037304 A | 2/2010 |

OTHER PUBLICATIONS

Bey, Alvin et al.: "The competition of trimethylhalosilanes and styrene for organolithium reagents." Journal of Organic Chemistry, 30 (7), pp. 2436-2440, 1965.
Gilman, Henry et al.: "Studies in the thianthrene system: Bromination and reductive bromination." Journal of the American Chemical Society, 77, pp. 5944-5948, 1955.
Lee, Doo-Yeon et al.: "Redox shuttle additives for chemical overcharge protection in lithium ion batteries." Korean Journal of Chemical Engineering, 19(4), pp. 645-652, 2002.
Liu, Jin-Gang et al.: "High refractive index polymers: fundamental research and practical applications." Journal of Materials Chemistry, 19, pp. 8907-8919, 2009.
Lovell, James M. et al.: "Synthesis of 1- and 2-substituted thianthrenes." Journal of Chemical Society, Perkin Transactions 1, 19, pp. 2391-2395, 1996.

*Primary Examiner* — Taofiq A Solola
(74) *Attorney, Agent, or Firm* — Seppo Laine Oy (57) ABSTRACT

Synthesis of thianthrene moiety containing silane and germane monomers and their polymerization is presented. The polymers show high refractive index, high transparency and excellent thermal stability. They are useful as dielectric films for semiconductor industry and for optical applications, including high-RI materials in CMOS image sensors.

6 Claims, 5 Drawing Sheets

ORGANOMETALLIC MONOMERS AND HIGH REFRACTIVE INDEX POLYMERS DERIVED THEREFROM

TECHNICAL FIELD

The present invention relates to organometallic monomers and to polymers derived from them. In particular, the invention concerns sulfurous monomers and high refractive index metalloid polymers, methods of producing novel monomers and the use of the polymers derived from them.

BACKGROUND ART

There is a need for high refractive index materials in the electronics industry. Such materials are widely used in flat panel displays, CCD and CMOS image sensors, for example in light pipe structures, microlenses, and as color filter overcoats, where use of high-RI materials results in improved angular response and increased overall quantum yield. In general, these materials need to have an index of refraction (RI) above 1.6, and they need to be sufficiently transparent in the visible wavelength range (400 to 800 nm). They also need to have proper gap-filling and planarizing properties, as well as good thermal stability. To withstand common processing steps, they should be curable to yield solvent resistant films, which have good adhesion on surrounding materials. They should also be suitable for chemical mechanical polishing (CMP).

Conventionally, aromatic polymers containing phenyl groups and higher aromatic ring systems such as naphthalene, phenanthrene, and anthacene moieties have been used for these applications. They have relatively high refractive indexes, said indexes amounting to values between 1.50 and 1.65. As a rule of thumb, the larger the ring system, the higher is the RI of the material. However, ring systems having more than three fused aromatic rings have a problem: they will begin to absorb blue light. As the blue channel is commonly the least sensitive of the three photosites in the RGB (red-green-blue) matrix, the materials cannot be used as high refractive optical materials without further compromising the blue light performance of CMOS image sensor.

There exist some high refractive index sulfur-containing polymers, such as thioethers and thiocarbonates (reference 1). However, aliphatic sulfur-containing polymers have relatively poor thermal stability. On the other hand, high refractive index polyimides, like polyimides in general, need curing temperatures above 300° C., typically 350° C., which is sometimes too much for CMOS devices. Polyimides also tend to have yellow cast, limiting further their use in optical applications.

For the above reasons, there is continued need for high refractive index transparent materials that can be cured at or below 250° C. but which are nevertheless thermally stable up to 450° C.

SUMMARY OF INVENTION

Technical Problem

It is an aim of the present invention to eliminate at least a part of the problems relating to the background art polymers for use in high refractive index materials and to provide monomers which can be used in the production of metalloid resins, such as polysiloxane or polygermoxane resins, having high RI and proper mechanical properties.

It is another aim of the present invention to provide novel polymers which have high RI and which can be used as high refractive optical materials, for example in CCD and CMOS image sensors, without compromising the blue light performance thereof.

It is still an aim of the invention to provide a novel method of producing novel sulfurous monomers at high yield.

It is a fourth aim of the invention to provide a method of producing novel polymers having improved properties suitable for use as high refractive optical materials.

Solution to Problem

In connection with the present invention it has been found that metalloid polymers, in particular polysiloxanes and polygermoxanes, bearing thianthrene units are highly transparent, thermally stable materials with high RI up to or above 1.73. They can be thermally cured at 200 . . . 400° C. to give solvent resistant film.

Surprisingly, the art is silent about silane and germane monomers or corresponding polymers containing a thianthrene moiety or skeleton. This may be due to lack of a suitable synthesis method for producing suitable monomers, such as 2-brominated thianthrenes, which—in turn—would be useful as starting materials for the polymerization processes. The best reported yields (32-47%, reference 2, for 2-bromothianthrene and 25%, reference 3, for 2,7-dibromothianthrene) so far published have been achieved by heating thianthrene in acetic acid with bromine several hours. Low reported yields results in prohibitively high price for the end product.

It has now surprisingly been found that the use of a combination of iodine and trifluoroacetic acid as a catalyst gives high yields of the desired products. The catalyst system also reduces the reaction temperature and the amount of bromine needed, resulting in further savings and reduced waste.

The novel silane and germane monomers are readily polymerized. Thus, for producing the novel polymers, in particular the silane or germane monomers bearing thianthrenyl group(s) and hydrolysable group or groups, such as methoxy, ethoxy, chlorine or bromine, are polymerized or copolymerized by hydrolysis and condensation polymerization, preferably in the presence of water and acid or base catalyst, to yield siloxane, germoxane or germo-siloxane or similar metalloid polymers.

More specifically, the monomers according to the present invention are characterized by what is stated in the characterizing part of claim 1.

The polymers according to the present invention are characterized by what is stated in the characterizing part of claim 7.

The method of producing monomers is characterized by what is stated in the characterizing part of claim 4 and the method of producing polymers is characterized by what is stated in the characterizing part of claim 12.

The novel uses are defined in claims 20 to 24.

Advantageous Effects of Invention

The present invention provides considerable advantages. Thus, thianthrene ring system has high refractive index due to both aromaticity and two sulfur atoms. Thianthrene is also highly transparent, and does not absorb light until UV-region below 300 nm. Being aromatic, it has high thermal stability. The polymers are useful as dielectric films for semiconductor industry and for optical applications. These siloxane and germoxane resins are also readily curable by heat, resulting in solvent resistant, cross-linked polymer films.

BRIEF DESCRIPTION OF DRAWINGS

Next the invention will be examined more closely with the aid of a detailed description and with reference to the attached drawings, in which.

DESCRIPTION OF EMBODIMENTS

As discussed above, the present invention provides high refractive index metalloid polymers, in particular siloxane or germoxane polymers, containing a thianthrene moiety attached to a silicon or germanium atom.

The polymer is preferably prepared by hydrolyzing and polymerizing thianthrene containing monomers, in particular thianthrene containing silane or germane monomers. Such monomers are exemplified by the following monomers having formulas I, II, III, IV, V and VI,

I

II

III

IV

V

VI wherein

Z is a metalloid, selected from silicon and germanium;

$A_1, A_2, A_3, A_4, A_5, A_6, A_7$ are independently selected from the group of hydrogen, linear or branched alkyl groups, in particular containing 1 to 6 carbon atoms, such as —$CH_3$, and —$CH_2CH_3$, aryl groups, such as phenyl, and halo groups, such as chloro, bromo or iodo, $R_1, R_2, R_3, R_4, R_5$, and $R_6$ are independently selected from the group of hydrogen, linear or branched alkyl groups, linear or branched alkoxy groups, halo groups, acycoxy groups, and aliphatic or aromatic cyclic groups, with the proviso that at least one of $R_1, R_2, R_3, R_4, R_5$, and $R_6$ is a hydrolyzable group.

The hydrolysable groups in the meaning of $R_1, R_2, R_3, R_4, R_5$, and $R_6$ are selected from halo, such as chloro and bromo, alkoxy groups having preferably 1 to 6 carbon atoms, such as methoxy, ethoxy, n-propoxy and isopropoxy, or acyloxy groups having 2 to 10 carbon atoms, such as acetoxy.

In the formulas above, at least one of $R_1, R_2, R_3, R_4, R_5$, and $R_6$ is a hydrolyzable group, preferably one of the above mentioned, typically at least two of $R_1, R_2, R_3, R_4, R_5$, and $R_6$ are hydrolyzable groups. In case there are two or more hydrolysable groups in the meaning of $R_1, R_2, R_3, R_4, R_5$, and $R_6$ then they can be the same or different, for example two alkoxy groups, two halo groups or one alkoxy and one halo group.

According to one preferred embodiment, all substituents $A_1, A_2, A_3, A_4, A_5, A_6, A_7$ stand for hydrogen.

In another embodiment, at least one of $A_1, A_2, A_3, A_4, A_5, A_6, A_7$ stands for a lower alkyl, such as methyl or ethyl or n- or isopropyl or i-, n- or t-butyl or chloro or bromo. In case of at least one bromo substitutent, the remaining bromo in the monomer can be alkylated by reaction with magnesium, iodomethane and a iron catalyst Fe(acac)3.

In a preferred embodiment, at least one, preferably several (2 to 6) of $R_1, R_2, R_3, R_4, R_5$, and $R_6$ stands for methoxy or ethoxy. However, in another embodiment, at least one of $R_1, R_2, R_3, R_4, R_5$, and $R_6$ can be methyl, vinyl or phenyl group.

If there is one metalloid atom, in particular silicon or germanium atom in the monomer, then at least one of $R_1, R_2, R_3, R_4, R_5$, and $R_6$ should be hydrolysable group.

As discussed above, neither silane or germane monomers nor the corresponding siloxane and germoxane polymers containing thianthrene moieties of the present kind are disclosed in the art, which may be caused by prior art problems relating to the synthesis of suitable starting materials. We have surprisingly found that by using a combination of iodine and trifluoroacetic acid as a catalyst, high yields of desired products will be reached. The catalyst system also reduces the reaction temperature and the amount of bromine needed, resulting in further savings and reduced waste.

An improved method according to the present invention for brominating thianthrene therefore comprises using elemental bromine and a catalytic amount of iodine and trifluoroacetic acid in an inert solvent. Thus, a modified silane or germane can be produced containing a thianthrene moiety by the steps of

- brominating thianthrene by using elemental bromine and a catalytic amount of both iodine and trifluoroacetic;
- recovering the brominated thianthrene thus obtained; and
- reacting the brominated thianthrene with a silane or with a germane.

In the present context, the terms silane and germane, respectively, are used with respect to compounds in which there is one or two metalloid atoms of the indicated kind, each of which contains four substituents.

In particular, it has been found that Grignard reagents prepared by reaction of bromothianthrenes with magnesium metal in suitable solvent, such as THF or diethyl ether, can be converted to thianthrenylsilanes and thianthrenylgermanes by coupling them with silane and germane compounds which bear hydrolysable groups, for example groups selected from halogens and alkoxy groups, to yield monomers having formulas I, II, III, IV, V and VI. Particularly suitable silane and germane compounds are presented below in formulas m-I to m-VI.

m-I m-II m-III m-IV m-V m-VI wherein each Z can be a metalloid, such as silicon or germanium;

each X can be the same or different and each X is independently a hydrolysable group. In particular, X stands for —OMe, —OEt, —OCOCH$_3$, —Cl, or —Br.

each Y can be the same or different and each Y is independently selected from H, methyl, ethyl, vinyl, allyl, phenyl, styryl, benzyl, naphthyl, phenanthrenyl, anthracenyl, or thianthrenyl groups; and B is a bridging group selected from bivalent hydrocarbyl residues, such as linear and branched alkylene groups, alkenylene groups, alkynylene groups, bivalent alicyclic groups, bivalent polycyclic groups, and bivalent aromatic groups (arylene groups), for example —CH$_2$—, CH$_2$CH$_2$—, CH$_2$CH$_2$CH$_2$—, arylene, and —C$_6$H$_4$—, and —C$_{10}$H$_6$— moieties.

It is known in the art that 1-substituted thianthrenes can be prepared via 1-lithiated thianthrene (cf. reference 4). Similar to Grignard reagents, organolithium reagents are also known to react with chlorosilanes to yield organosilanes (cf. reference 5). However, the references are silent about the provision of polymerizable silane or germane monomers containing a thianthrene residue.

Starting from the novel thianthrene silanes and/or germanes, a high refractive index siloxane or germoxane polymer can be obtained which contains thianthrene moieties attached to silicon or germanium atoms in the siloxane or germoxane backbone of the polymer.

The polymers of the invention are illustrated by schematic formulas XIII and XIV

XIII

XIV

Ax = —H, —CH₃, CH₂CH₃, phenyl, —Cl, —Br, or —I
Z = Si or Ge
n = 3...30,000

It should be noted that the legends given below the formulas only represent examples of preferred embodiments and are not to be given a restrictive interpretation.

The mass-average molecular weight (Mw) of the thianthrene bearing polysiloxane and polygermoxane is preferentially in the range of 500 to 10,000,000 g/mol, for example 750 to 5,000,000 g/mol, in particular 1000 to 1,000,000 g/mol, typically 1500 to 500,000 g/mol.

The thianthrene ring system has high refractive index due to both aromaticity and two sulfur atoms. Thianthrene is also highly transparent, and does not absorb light until UV-region below 300 nm. Being aromatic, it has high thermal stability.

The polymer is typically prepared by hydrolyzing and polymerizing thianthrene containing silane or germane monomers. Optionally, a copolymer is produced by co-hydrolyzing and polymerizing thianthrene containing silane or germane monomers with one or more other silane or germane monomers. Naturally, it is possible to prepare germano-siloxane mixed metal copolymers by co-hydrolysing silane and germane monomers simultaneously.

Thus, the terms "siloxane polymer", "germoxane polymer" and "germano-siloxane" are to be interpreted to cover homopolymers of monomers of the indicated kind as well as copolymers formed by silane and germane monomers of the indicated kind, for example of Formulas I to VI, co-hydrolyzed with one or more other silane or germane monomers.

Examples of the latter kind of comonomers are presented by the formulas VII to XII

VII

VIII

IX

X

XI

XII wherein
each Z is a metalloid atom selected from silicon and germanium;
each X can be the same or different and each X is independently a hydrolysable group;
each Y can be the same or different and each Y is independently selected from H, methyl, ethyl, mercaptopropyl, vinyl, allyl, phenyl, styryl, benzyl, naphthyl, phenanthrenyl, anthracenyl, glycidyloxypropyl, acryloxypropyl, methacryloxypropyl, or thianthrenyl groups; and
B is a bridging group selected from bivalent hydrocarbyl residues, such as linear and branched alkylene groups, alkenylene groups, alkynylene groups, bivalent alicyclic groups, bivalent polycyclic groups, and bivalent aromatic groups (arylene groups), for example —CH₂—, CH₂CH₂—, CH₂CH₂CH₂—, arylene, and —C₆H₄—, and —C₁₀H₆— moieties.

Generally, the molar ratio between the silane and germane monomers in the production of germano-siloxane copolymers can vary broadly in the range of 1:1000 to 1000:1, in particular 1:100 to 100:1, for example about 100:1 to 1.1:1 (silanegermane monomers, a majority of the copolymer being made up by the silane).

The hydrolysable group X of formulas VII to XII can be independently selected from halo, such as chloro and bromo, alkoxy groups, such as methoxy, ethoxy, n-propoxy, isopropoxy, and acyloxy groups, such as acetoxy. In particular, X stands for —OMe, —OEt, —OCOCH₃, —Cl, or —Br.

The silane and germane monomers bearing at least one thianthrenyl group and at least one hydrolysable group, such as methoxy, ethoxy, chlorine or bromine, can be polymerized in the presence of water and acid or base catalyst, to yield siloxane and germoxane polymers.

The acid can be any acid which is strong enough to cause the hydrolysis of the hydrolysable group. Examples of such acids are hydrochloric acid, nitric acid, trifluoroacetic acid, sulfuric acid, phosphoric acid and perchloric acid.

The base catalyst can be tetra-alkylammonium hydroxide, an alkali metal hydroxide, or an amine base such as but not limited to 1,8-diazabicycloundec-7-ene (DBU). Also super bases such as phosphazenes, amidines and guanidines can be used.

The polymerization or copolymerization reaction can be run neat, but solvents can be added such as, but not limited to, THF, 2-methyl tetra hydrofuran, 2-(methoxymethyl)tetrahydrofuran, acetone, MEK, methanol, ethanol or isopropanol, to facilitate proper stirring. The reaction can be run at −20 . . . 200° C.

Usually the reaction is run either at room temperature or at elevated temperature by refluxing the reaction solution.

The reaction time can vary from few minutes to one week, depending on the reaction conditions and monomer used. The monomers can be added all at once, or one or more monomers can be first prehydrolyzed before addition of other monomers. This is often advantageous if the reactivities of the monomers towards hydrolysis differ greatly between the monomers.

After the hydrolysis reaction, the molecular weight of the polymer can be further increased by controlled base catalyzed condensation reaction, such as by refluxing it in THF using 1% triethylamine as the basic catalyst. Alternatively, the molecular weight can also be increased just by refluxing it in high boiling solvent such as but not limited to propylene glycol methyl ether acetate until desired molecular weight is achieved.

The polymer can be provided in the form of a polymer solution; the provision of such a solution is interesting because a polymer film can easily be prepared from the polymer solution.

The polymer solution preferably contains the polymer, a solvent, an optional surfactant, an optional photo acid generator (PAG), photo base generator (PBG), or photo radical generator (PRG), and optionally nanoparticles consisting of metal oxide nanoparticles, sulfide nanoparticles, nanodiamonds, carbon nanotubes, amorphous silicon nanoparticles or any mixture thereof.

The metal oxide or metal sulfide nanoparticles are preferably selected from the group of $ZrO_2$, $TiO_2$, $HfO_2$, $SiO_2$, $SnO_2$, $Al_2O_3$, $CeO_2$, $Y_2O_3$, $ZnO$, $BaTiO_3$, $Nb_2O_5$, $GeO_2$, $Sb_2O_3$, $Ta_2O_3$, $La_2O_3$, $WO_3$, $Bi_2O_3$, $PbO$, $ZnS$, $CdS$, $PbS$.

The solvent can be selected from propylene glycol methyl ether acetate, dipropylene glycol methyl ether acetate, n-methyl-2-pyrrolidone, anisole, benzyl alcohol, toluene, ethylbenzene, xylene, mesitylene, dimethylacetamide, dimethylformamide, 1,3-dimethyl-3,4,5,6-tetrahydro-2(1H)-pyrimidinone, hexamethylphosphoramide, propylene glycol methyl ether, propylene glycol ethyl ether, propylene glycol propyl ether, methyl lactate, ethyl lactate, propyl lactate, ethyl acetate, propyl acetate, butyl acetate, cyclopentanone, cyclohexanone, dimethylsulfoxide, methyl isobutyl ketone, methyl ethyl ketone, methyl propyl ketone, 2-heptanone, gamma-butyrolactone, ethyl 3-ethoxypropionate, ethyl 3-methoxypropionate, ethyl pyruvate, ethyl cellosolve acetate, tetrahydrofurfuryl alcohol, 2-(methoxymethyl)tetrahydrofuran, 2-methyl tetrahydrofuran, tetrahydrofuran, isopropanol, butanol, anisole or any mixtures thereof.

The optional surfactant of the polymer solution is selected from fluorosurfactants, siloxane surfactants and alkylphenol ethoxylate surfactants.

The present polymers can be used in CMOS and CCD image sensors as a high refractive index material. Other applications include the use
- in the semiconductor industry as a dielectric material;
- in various optical devices as a high refractive index material;
- in light emitting diodes as high refractive index material; and
- in flat panel displays as high refractive index material.

Next the invention will be examined more closely with the aid of a number of non-limiting working examples.

EXAMPLES

Example 1

Thianthrene (21 g, VWR International) was placed in a 250 mL rb flask along with dichloromethane (DCM, 150 mL) and trifluoroacetic acid (TFAA, 6 mL). A small amount of iodine (0.4 g) was added, and bromine (19 g) was metered in. The reaction was allowed to proceed for 24 hours at +23° C. It was then taken to rotary evaporator and DCM was removed at 45° C./40 mbar and recycled (over 90%) for a new batch without reduction in yield. Toluene (100 mL) was added, and evaporation was continued until no vapors came out at 60° C./15 mbar. A light red viscous material remained, which started crystallizing slowly upon cooling.

Example 2A

Molecular Weight: 378.581

The material from example 1 was dissolved in dry THF (150 mL), and chlorotriethoxysilane (21 g) and magnesium turnings (4 g) were added. The flask was heated to reflux, until the reaction started. After 2 hours reaction, GC/MS was run of the reaction solution, which showed that there was 2.3% thianthrene, 86.0% 2-(triethoxysilyl)thianthrene and 3.5% 2,8- and 2,7-bis(triethoxysilyl)thianthrene formed. Hexanes (100 mL) was added to the solution to precipitate magnesium salts. The liquid was taken to rotary evaporator, and volatiles were removed at 60° C./20 mbar. The product 2-(triethoxysilyl)thianthrene was distilled under vacuum, bp. 190° C./0.1 mbar, Yield 12.4 g (purity 98.6% by GC/MS) as colorless liquid which crystallized slowly upon standing overnight.

Example 2B 2-(Triethoxysilyl)thianthrene (5 g) from example 2A was dissolved in acetone (2.5 mL). One drop of trifluoroacetic acid and two drops of 0.5% HCl were added. DIW (1.5 g) was slowly dripped in. The solution was heated at 65° C. for two hours. DIW (10 mL) and methyl t-butyl ether (30 mL) were added. The organic phase was separated and vacuum-dried in rotary evaporator (60° C./15 mbar). The resulting white solid polymer (4.5 g, Mw/Mn=1,221/1,033 by GPC) was dissolved in MEK (21 g), surfactant (45 mg, BYK®306 by BYK Chemie GmbH) was added, followed by filtration through a 0.2μ PTFE filter. The solution was spin coated on a silicon wafer at 1000 rpm, followed by soft bake at 150° C./5 min and cure at 200 to 240° C. for 10 min under nitrogen. A 752 nm crack-free and defect-free film with RI=1.72 was obtained. The film was soaked in acetone (30 min, 23° C.) without change to its thickness, RI or other properties. The film was also baked at 400° C./5 min/argon, and only 2.8% thickness-loss was seen with no impact on RI or transmittance, which was >95% over the visible wavelength. Scotch-tape test was passed, indicating good adhesion between the polymer and silicon wafer.

Figure 1:
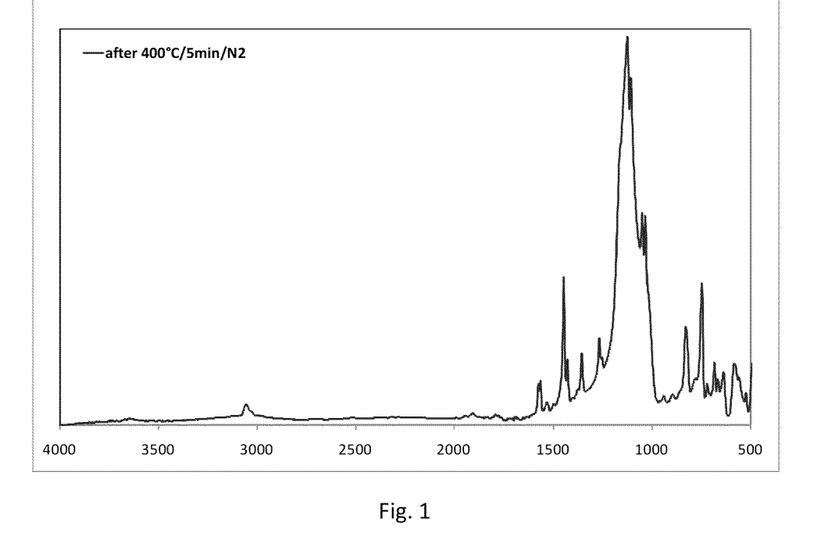
FIG. 1 shows the FTIR spectrum of the film obtained in Example 2B.
Figure 2:
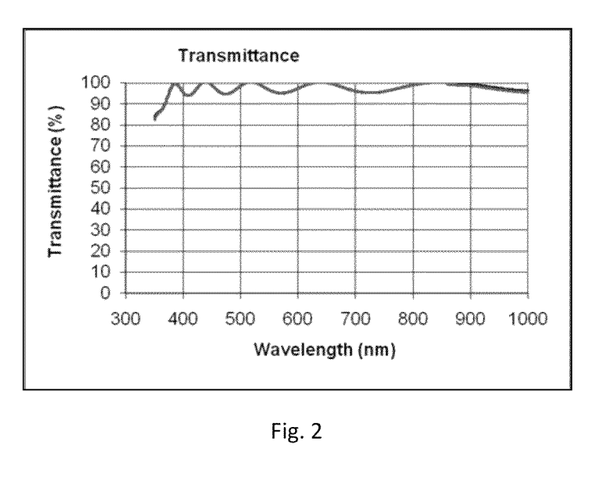
FIG. 2 shows t Transmittance spectrum of the film obtained in Example 2B after 400° C./5 min cure.

FIG. 1 shows the FTIR spectrum of the film thus obtained; the transmittance spectrum of the film is shown (as a function of wavelength) in FIG. 2. The data for the latter figure were measured after curing the film for 5 min at 400° C.

Figure 3:
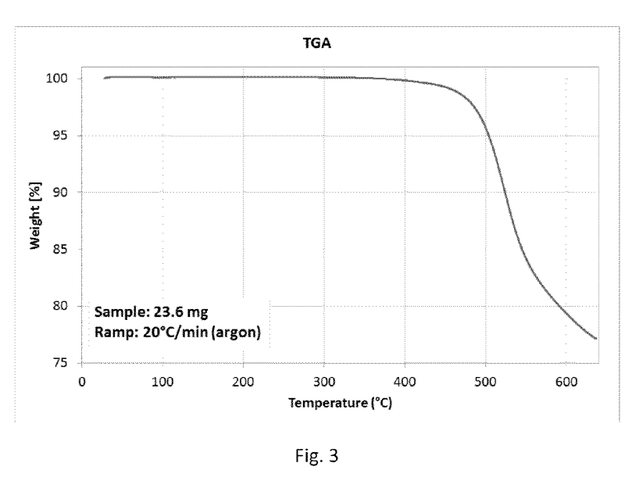
FIG. 3 shows the TGA curve of the cured polymer of example 2B. T(m-5%) is 504° C.

The material also showed excellent thermal stability by TGA, where 95% of sample mass remained up to 504° C. in inert atmosphere. This demonstrates that thianthrene-based siloxanes can give high refractive index, colorless and highly thermally stable films, which are suitable for optical application. Dielectric constant k=3.52 was measured for the film. FIG. 3 shows the curve for the TGA of the cured polymer; T (m-5%) is 504° C.

Figure 4:
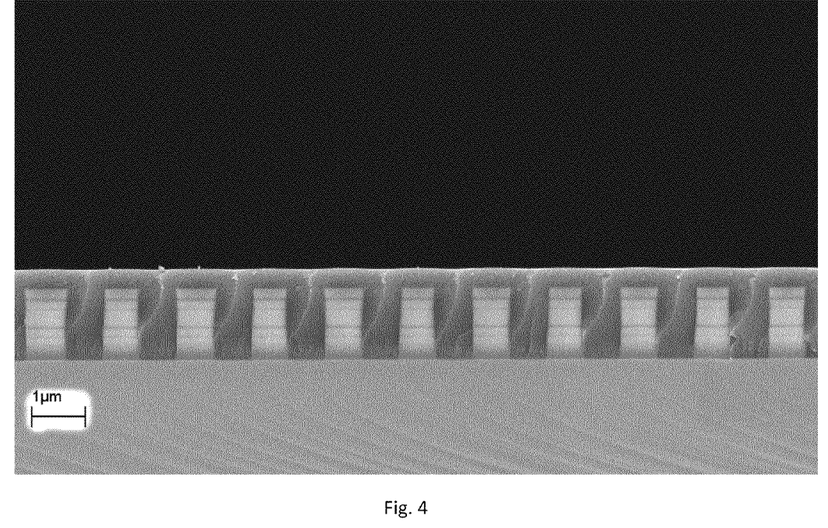
FIG. 4 shows the SEM of the gap-fill of polymer example 2B on a structured silicon wafer.

FIG. 4 shows the SEM of the gap-fill of a polymer according to the present example on a structured silicon wafer.

Example 2C

The solid polymer (1 g) from example 2B was dissolved in MEK (1 g), and the solution was refluxed at 100° C. for five hours. Molecular weight could be increased this way to Mw/Mn=3,171/2,090.

Example 2D

Figure 5:
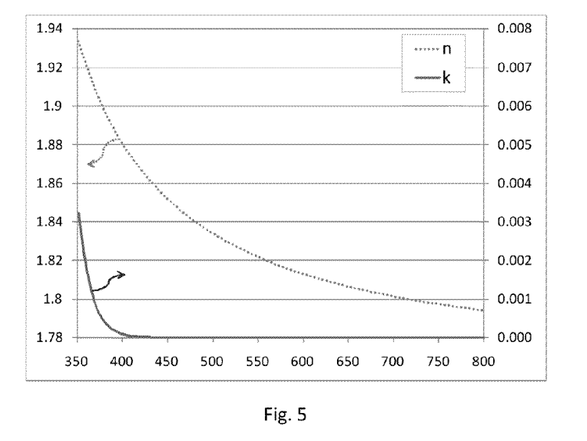
FIG. 5 shows N & k values as a function of wavelength of the polymer film of Example 2D.

The polymer from example 2B (1 part) was dissolved in diethyl ketone (10 parts), and $ZrO_2$-nanoparticles (1 part, Conventional $ZrO_2$ dispersion, Sumitomo Osaka Cement Co., Ltd.) were added, and the solution was evaporated to ~10% solid content. The solution was filtered through a 0.2 μm PTFE-filter, and spin-coated on a silicon wafer, followed by curing on a hotplate at 200 to 240° C. for 10 mins under nitrogen. A 262 nm thick film with RI=1.809 at 630 nm was obtained. The film had no absorption between 400 . . . 800 nm as can be seen from FIG. 5 showing the N and k values as a function of wavelength of the polymer film.

Example 2E

Figure 6:
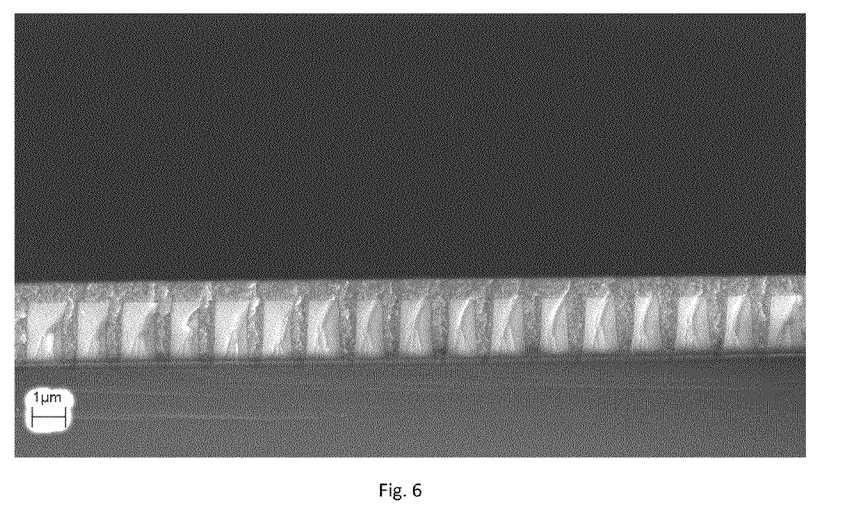
FIG. 6 shows the SEM of the gap-fill of the material having 75% $TiO_2$ nanoparticles from Example 2E on a structured silicon wafer.

The polymer from example 2B (1 part) was dissolved in MEK (6 parts), and $TiO_2$-nanoparticles (3 parts, NanoGram nSol-101-20B) were added, and the solution was evaporated to 16% solid content. The solution was filtered through a 0.2 μm PTFE-filter, and spin-coated on a silicon wafer and a glass plate, followed by curing on a hotplate at 250° C./5 min/N2. A 626 nm thick, colorless and clear film with RI=1.915 at 630 nm was obtained. FIG. 6 shows the SEM of the gap-fill of the material containing 75% $TiO_2$ nanoparticles on a structured silicon wafer.

Example 3A

Thianthrene (103.1 g) was dissolved in DCM (690 g) and trifluoroacetic acid (21 g). Iodine (0.4 g) was added, along with bromine (95.5 g, 1.25 ekv). The reaction was allowed to proceed for 1 day at 23° C., followed by 1 day at 4° C. The solution was taken to rotary evaporator, and volatiles were removed at 40° C./20 mbar. Toluene (100 mL) was added, and evaporation continued for 1 hour at 5 mbar/60° C. GC/MS showed the following composition: Thianthrene (2.14%), 2-bromothiathrene (83.75%) and dibromothianthrene (14.11%, total of the 2,7- and 2,8-isomers). The dark red material was dissolved in dry THF (50 mL) for the next reaction step.

Example 3B

A 3-neck 3 L flask was filled with magnesium turnings (20 g), THF (650 g) and chlorotriethoxysilane (146 g), and heated to reflux. 2-Bromothianthrene from Example 3A was added to the flask in small portions. Grignard started instantly. The reaction was allowed to cool for 1 hour, after which magnesium salts were precipitated with hexanes (500 mL). The solution was filtered, followed by evaporation of volatiles by rotary evaporator. The material was distilled twice at 190 . . . 200° C./<1 mbar, giving colorless 2-(triethoxysilyl) thianthrene (125.9 g, 69.8% overall yield based on thianthrene, purity >99% by GC/MS).

Example 4A

Thianthrene (200 g) was dissolved in DCM (1000 g) and trifluoroacetic acid (25 g). Iodine (1 g) was added, along with bromine (161.30 g). The reaction was allowed to proceed for 1 day at 23° C., followed by 9 days at 4° C. GC/MS showed the following composition: Thianthrene (2.34%), 2-bromothiathrene (90.49%) and dibromothianthrene (7.17%, total of the 2,7- and 2,8-isomers). This corresponds to 91% theoretical yield of monobrominated product. The solution was taken to rotary evaporator, and volatiles were removed at 40° C./20 mbar. Toluene (2×100 mL) was added, and evaporation continued for 1 hour at 5 mbar/60° C. The material crystallized in rotary evaporator as yellow solid. It was dissolved in dry THF (300 mL) for the next reaction step.

Example 4B

A 3-neck 3 L flask was filled with magnesium turnings (35 g), THF (600 g) and chlorotriethoxysilane (278 g), and heated to reflux. Bromothianthrene solution from Example 4A was added to the flask in small portions. Grignard started instantly. The reaction was allowed to cool for 1 hour, after which magnesium salts were precipitated with heptanes (500 mL). The solution was filtered, followed by evaporation of volatiles by rotary evaporator. The material was distilled twice at <1 mbar, giving colorless 2-(triethoxysilyl)thianthrene (bp. 175 . . . 200° C., 234.2 g, 66.9% overall yield based on thianthrene, purity 99.5% by GC/MS) and bis(triethoxysilyl)

thianthrene (bp. 200 . . . 225° C., 26.7 g, purity 94.6% by GC/MS, a mixture of 2,7- and 2,8-isomers, yield 5.3% by GC/MS).

Example 4C

The mixture of 2,7- and 2,8-bis(triethoxysilyl)thianthrene from Example 4B (6 g) was dissolved in acetone (6 g). Three drops of trifluoroacetic acid was added, and DIW (3 g) was slowly added while stirring. A clear transparent solution was obtained. It was heated at 65° C. for one hour, after which PGMEA was added (60 g). The solution was evaporated in rotary evaporator until 27 g solution with solid content of 13.97% was obtained. GPC (in THF) gave molecular weight MwMn=27,353/4,838. The solution was spin-coated on a silicon wafer at 2,000 rpm and softbaked at 250° C./5 min/N2, followed by the cure at 400° C./5 min/N2. The cured film was colorless and free from defects, and had thickness of 499 nm and RI=1.665. Shrinkage between soft bake and cure was 2 percent.

Example 5

Figure 7:
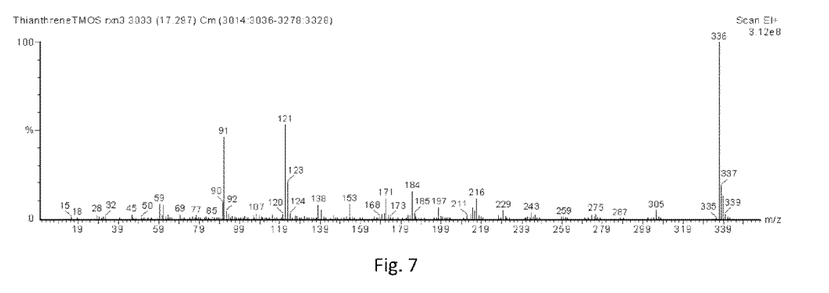
FIG. 7 shows the mass spectrum of 2-(trimethoxysilyl)thianthrene.

A 3-neck 1 L flask was filled with magnesium turnings (5 g), THF (200 g) and tetramethoxysilane (50 g), and heated to reflux. 2-Bromothianthrene (40 g), prepared analogously to Example 3A was added to the flask in 10 g portions. Grignard started within 10 minutes. The reaction was allowed to cool for 1 hour, after which magnesium salts were precipitated with hexanes (200 mL). GC/MS of the solution showed that along with some thianthrene, 2-(trimethoxysilyl)thianthrene was obtained in ~60% yield (FIG. 7).

Example 6

Figure 8:
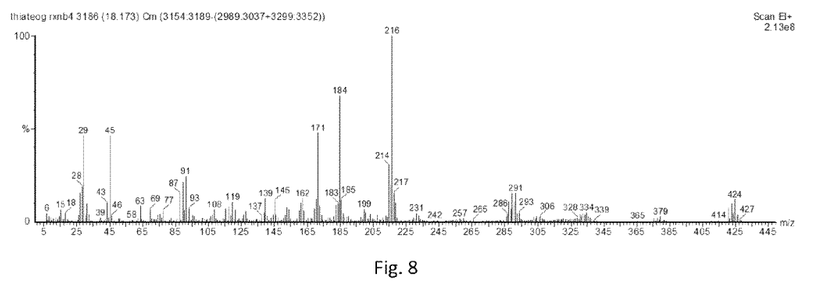
FIG. 8 shows the mass spectrum of 2-(triethoxygermyl)thianthrene.

A 3-neck 500 mL flask was filled with magnesium turnings (8 g), THF (100 g) and tetraethoxygermane (35 g), and heated to reflux. Crude 2-bromothianthrene (30 g) from Example 1 was added to the flask in small portions. Grignard started after a few minutes and kept refluxing by its own heat for ten minutes. The reaction was allowed to cool for 1 hour, after which magnesium salts were precipitated with heptanes (300 mL). The solution was filtered, followed by evaporation of volatiles by rotary evaporator. The material was distilled three times at <1 mbar, giving colorless 2-(triethoxygermyl)-thianthrene (bp. 180 . . . 210° C., 11 g, 30.5% overall yield based on 2-bromothianthrene, purity 99.5% by GC/MS). FIG. 8 shows the mass spectrum of the compound.

Example 7

Figure 9:
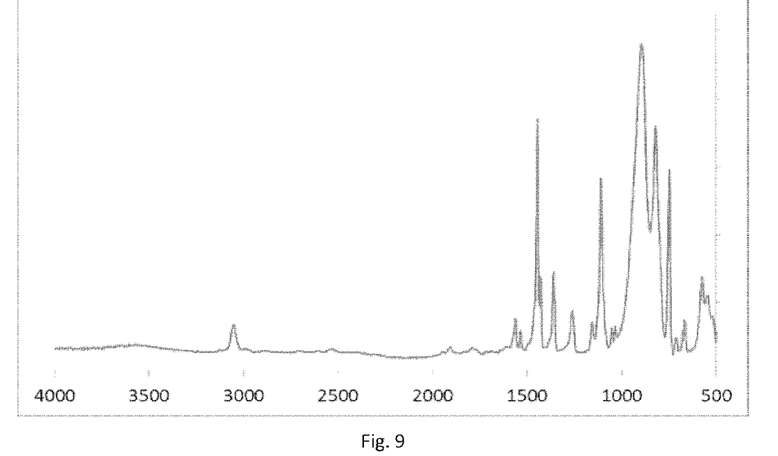
FIG. 9 shows the FTIR spectrum of the film obtained in Example 7.
Figure 10:
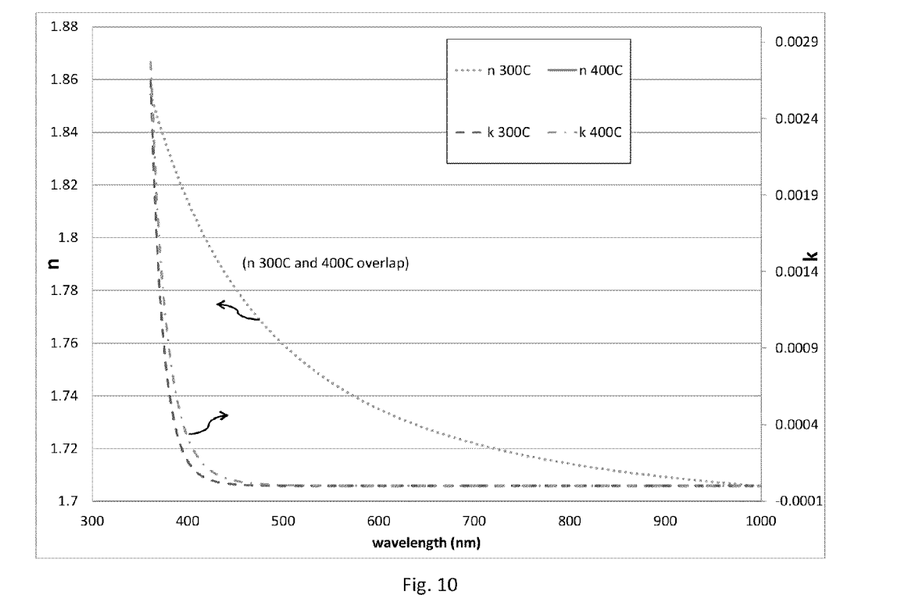
FIG. 10 shows N & k values as a function of wavelength of the polymer film of Example 7.
Figure 11:
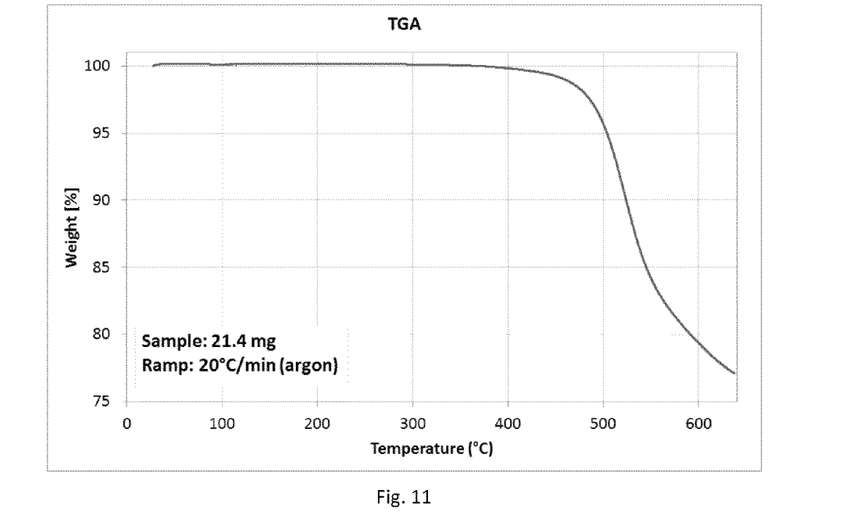
FIG. 11 shows the TGA curve of the cured polymer of Example 7.

2-(Triethoxysilyl)thianthrene (1 g) was dissolved in 2-(methoxymethyl)tetrahydrofuran (5 g). While vigorously stirring, 0.01M HCl (20 mg) and DIW (100 mg) were added, and the resulting sol-gel was allowed to react for 30 minutes. Surfactant (BYK 307, 4 mg) was added and the solution was filtered through a 0.2 μm PTFE-filter. It was spin casted on a silicon wafer and cured at 250° C. for 5 min. A solvent resistant transparent film was obtained having thickness of 606 nm and refractive index of 1.73. FTIR of the film is shown in FIG. 9. The film was further heated at 300 and 400 both for 5 minutes and n&k values were measured (FIG. 10). Low absorption and high RI were observed for both temperatures indicating no tendency for yellowing. The cured film passed Scotch-tape test after each temperature. TGA of the film after the 250° C. cure is presented in FIG. 11.

Example 8

A 3-neck 500 mL flask was filled with magnesium turnings (8 g), THF (100 g) and tetraethoxygermane (35 g), and heated to reflux. 9-Bromophenanthrene (30 g) was added to the flask in small portions. Grignard started after a few minutes and kept refluxing by its own heat for ten minutes. The reaction was allowed to cool for 1 hour, after which magnesium salts were precipitated with heptanes (300 mL). The solution was filtered, followed by evaporation of volatiles by rotary evaporator. The material was distilled three times at <1 mbar, giving colorless 9-(triethoxygermyl)phenanthrene (bp. 170 . . . 190° C., 21 g, 46.7% overall yield based on 2-bromophenanthrene, purity 99.5% by GC/MS).

2-(Triethoxysilyl)thianthrene (1 g) was dissolved in n 2-(methoxymethyl)tetrahydrofuran (5 g). Dilute hydrochloric acid (0.01M, 300 mg) was added, and the monomer was allowed to hydrolyze for 30 min. Then, 9-(triethoxygermyl) phenanthrene (1 g) was added, and the polymerization was allowed to proceed for another 30 mins. The solution was diluted with 2-(methoxymethyl)tetrahydrofuran (5 g), surfactant was added (BYK 307, 10 mg), and the polymer solution was finally filtered through a 0.2 µm PTFE-filter. After coating the solution on a silicon wafer followed by the cure at 250 for 5 mins, a transparent film with thickness of 581 nm and RI=1.721 was obtained. This example illustrates the synthesis of mixed metal germano-siloxane co-polymer of a thianthrene silane with a germane monomer.

INDUSTRIAL APPLICABILITY

The present polymers have high refractive index, high transparency and excellent thermal stability. They are useful as dielectric films for semiconductor industry and for optical applications, including high-RI materials in CMOS image sensors.

CITATION LIST

1. Ueda, M., et al., J. Mater. Chem., 2009, 19, 8907-8919
2. H. Gilman et al., J. Am. Chem. Soc., 77, 5944-8 (1955)
3. D-Y Lee et al., Korean J. Chem. Eng., 19(4), 645-652 (2002)
4. Joule, J. A., et al., J. Chem. Soc., Perkin Trans. 1, 1996, 2391-2395
5. Weyenberg, D. R., et al., J. Org. Chem., 1965, 30 (7), pp 2436-2440

The invention claimed is:

1. Thianthrene containing metalloid monomer of one of formulas I, II, III, IV, V and VI, -continued wherein Z is a metalloid selected from silicon and germanium;

$A_1, A_2, A_3, A_4, A_5, A_6, A_7$ are independently selected from the group of hydrogen, linear or branched alkyl groups, aryl groups, and halo groups; and

$R_1, R_2, R_3, R_4, R_5,$ and $R_6$ are independently selected from the group of hydrogen, linear or branched alkyl groups, linear or branched alkoxy groups, halo groups, acyloxy groups, and aliphatic or aromatic cyclic groups, with the proviso that at least one of $R_1, R_2, R_3, R_4, R_5,$ and $R_6$ is a hydrolyzable group selected from halo groups, alkoxy groups, and acyloxy groups.

2. The monomer according to claim 1, wherein $A_1, A_2, A_3, A_4, A_5, A_6, A_7$ are independently selected from the group of hydrogen, linear or branched alkyl groups containing 1 to 6 carbon atoms, aryl groups, and halo groups.

3. A high refractive index siloxane or germoxane polymer of thianthrene moieties attached to silicon or germanium atoms, wherein the thianthrene moieties are obtained from removing the hydrolysable group of thianthrene containing metalloid monomers of one of formulas I, II, III, IV, V and VI, wherein Z is a metalloid selected from silicon and germanium;

$A_1, A_2, A_3, A_4, A_5, A_6, A_7$ are independently selected from the group of hydrogen, linear or branched alkyl groups, aryl groups, and halo groups; and $R_1, R_2, R_3, R_4, R_5,$ and $R_6$ are independently selected from the group of hydrogen, linear or branched alkyl groups, linear or branched alkoxy groups, halo groups, acyloxy groups, and aliphatic or aromatic cyclic groups, with the proviso that at least one of $R_1, R_2, R_3, R_4, R_5,$ and $R_6$ is a hydrolyzable group selected from halo groups, alkoxy groups, and acyloxy groups.

4. The monomer according to claim 1, wherein the halo groups are chloro or bromo groups, wherein the alkoxy groups have 1 to 6 carbon atoms and are methoxy, ethoxy, n-propoxy and isopropoxy groups, and wherein the acyloxy group has 2 to 10 carbon atoms and is an acetoxy group.

5. The polymer according to claim 3, wherein the halo groups are chloro or bromo groups, wherein the alkoxy groups have 1 to 6 carbon atoms and are methoxy, ethoxy, n-propoxy and isopropoxy groups, and wherein the acyloxy group has 2 to 10 carbon atoms and is an acetoxy group.

6. The polymer according to claim 3, wherein $A_1$, $A_2$, $A_3$, $A_4$, $A_5$, $A_6$, $A_7$ are independently selected from the group of hydrogen, linear or branched alkyl groups containing 1 to 6 carbon atoms, aryl groups, and halo groups.

* * * * *